United States Patent [19]

Baumgartner

[11] 4,069,077
[45] Jan. 17, 1978

[54] TOWEL TABBING MACHINE AND METHOD

[75] Inventor: Frank Baumgartner, Jamesburg, N.J.

[73] Assignee: Pacon Manufacturing Corporation, Metuchen, N.J.

[21] Appl. No.: 723,683

[22] Filed: Sept. 16, 1976

[51] Int. Cl.² ............................................. B32B 31/00
[52] U.S. Cl. .................................... 156/152; 156/265; 156/269; 156/510; 156/519
[58] Field of Search ............... 156/152, 519, 269, 265, 156/510, 554; 93/1 TS, 8 WA; 428/202, 343, 40, 352, 354, 191; 128/132 D, 292, 156

[56] References Cited

U.S. PATENT DOCUMENTS

| | | | |
|---|---|---|---|
| 2,608,503 | 8/1952 | Meyer | 156/519 |
| 3,245,855 | 4/1966 | Stenvall | 156/152 |
| 3,322,600 | 5/1967 | Harrison et al. | 156/519 |
| 3,847,702 | 11/1974 | Jones | 156/269 |
| 3,897,293 | 7/1975 | Babcock | 156/519 |

Primary Examiner—Douglas J. Drummond
Attorney, Agent, or Firm—Behr & Woodbridge

[57] ABSTRACT

A tabbing machine is employed to place a tab between the release layer and the adhesive layer of an adhesive strip. The adhesive layer of the adhesive strip is double backed and adapted to be placed upon a surgical towel or the like. The tab allows the user of the towel to readily grasp the release layer and remove the same without inadvertently tearing the underlying adhesive layer which is attached to the towel. Two layer adhesive tape is initially fed to a roll wherein the double backed adhesive layer is separated from the release layer. The release layer and the adhesive layer are subsequently reunited at a nip point where a tab is inserted. The tab is then sandwiched between the release layer and the adhesive layer. The tape is subsequently applied to a surgical towel and then cut at the location of the tab. In this manner, the but tab forms the trailing tab of one towel and the leading tab of the other.

9 Claims, 6 Drawing Figures

TOWEL TABBING MACHINE AND METHOD

BACKGROUND OF THE INVENTION

1. Field of the Invention

This invention relates to a machine and method for applying tabs between the release layer and the adhesive layer of an adhesive strip of the sort associated with surgical towels.

2. Description of the Prior Art

The use of adhesive strips on surgical towels is known to those of ordinary skill in the art.

CROSS REFERENCE TO RELATED APPLICATIONS

A towel of the sort manufactured by the machine described herein is disclosed in a copending U.S. patent application Ser. No. 722,980 entitled "Tabbed Towel" by Arthur Shannon, Sr. For example, Kelly, U.S. Pat. No. 3,916,887 discloses a "Surgical Drape with Adhesive On Top and Bottom" wherein the drape includes a tab located between an adhesive layer and a release layer. The Kelly invention, however, is fundamentally different from the towel of the present invention in that the tab is very long and runs the width of the drape. Other towels of interest are disclosed in the following patents: Hoff, U.S. Pat. No. 3,470,590; Mesek et al, U.S. Pat. No. 3,840,013; and Krebs et al, U.S. Pat. No. 3,930,497.

Towels similar in structure to that manufactured by the invention described herein were previously made by hand. Tabs like small address labels were inserted manually between the release layer and one side of the double backed tape. There were several disadvantages to this prior art method. First of all, being manual the method was labor intensive and therefore expensive. Second of all, the release tab frequently overlapped the adhesive layer thereby consuming more tab stock than necessary. Thirdly, the registration between the tab and the adhesive tape is not as good as could be achieved by automated methods.

There are some machines known in the prior art which will insert a first material between two layers of a second material. For example, Wang, U.S. Pat. No. 2,995,174 discloses a method of inserting a clip between two layers of bag material. Van Cleff, U.S. Pat. No. 2,248,318 and Beck, U.S. Pat. No. 3,298,891 also disclose prior art machinery of interest. However, none of the prior art appears to disclose an automatic method for inserting a tab between the release layer and the adhesive layer of adhesive tape stock. In particular the prior art does not disclose the subsequent applying of such stock to a surgical towel and the cutting of the same at the location of the tabs so as to form a front and back tab on the leading and trailing edges of the towel.

SUMMARY OF THE INVENTION

Briefly described the present invention comprises an automatic method and apparatus for applying tabs to a surgical towel or drape. The tab is located between the release layer and the adhesive layer of adhesive tape at the leading and trailing edges of the towel. The towel is formed on a machine equipped with a tabbing device. Towel stock is fed to the towel forming machine and folded lengthwise so as to have certain predetermined dimensions. Simultaneously adhesive tape having a double sided adhesive layer and a release layer is fed to the machine. The release layer is separated from the adhesive layer and then subsequently reunited. Just before the adhesive layer and the release layer are reunited a small tab of material is inserted between the two layers. The reunited adhesive tape with the tabs sandwiched between the two layers at predetermined intervals is then applied to the towel stock in a longitudinal direction. A cutting mechanism severs the towel stock and the adhesive tape at a point intermediate the tab locations, thereby forming a release tab at the leading and trailing edges of the towel. The apparatus also includes a feature which permits timing adjustments to be made between the insertion of the tab and the cutting of the towel so that the cutting takes place at the exact midpoint of the inserted tab. These and other features of the present invention will be more fully understood with reference to the following drawings and detailed description of the invention.

BRIEF DESCRIPTION OF THE DRAWINGS

FIG. 2b is a detailed view of one of the tab sections of the towel illustrated in FIG. 2a.

DETAILED DESCRIPTION OF THE INVENTION

During the course of this description like numbers will be used to designate like elements according to the different figures illustrating the invention.

Figure 1:
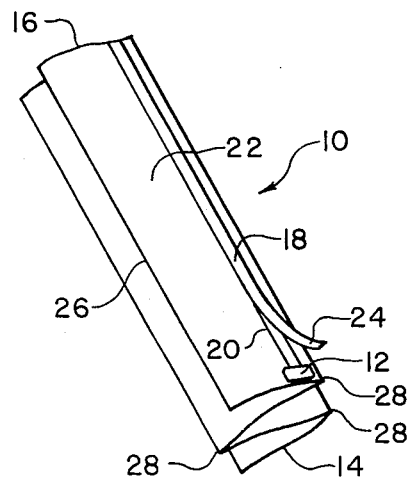
FIG. 1 is a perspective view of a prior art towel having manually attached tabs.

FIG. 1 illustrates a prior art towel 10 which includes a manually attached tab 12 at the leading edge 14 of the towel. There is no tab at the trailing edge 16 of the towel. The tab 12 covers the leading edge of a double backed adhesive layer 20. Adhesive layer 20 has adhesive on both sides such that it will stick to the towel stock 22. A backing release paper 18 also sticks to the adhesive layer 20 but with very little force. Accordingly, the release layer 18 can be easily stripped away from the double adhesive layer 22. The towel can then be attached to the object which it is meant to protect. Typically, such a towel is used to cover a patient during a surgical operation and also serves as a clean field upon which the surgeon may operate. The tab 12 is located adjacent to the leading edge 14 and directly between the lower adhesive layer 20 and the top release layer 18. Tab 12 sticks to the lower adhesive layer 20 but does not adhere to the upper release layer 18. Therefore a small leading portion 24 of the upper release layer 18 always projects above the plane of the towel 22. It is relatively easy for the user of the towel to grab the release layer 18 by the front portion 22 and strip the release layer 18 away from the adhesive backing 20. This renders the towel readily usable for its purpose. According to the preferred embodiment of the present invention the adhesive layer 20 and the release layer 18 run in a direction parallel to the side edge 26 of the towel. It therefore follows that the adhesive layer 20 and the release layer 18 run in a direction parallel to the longitudinal folds 28 in the towel.

The prior art towel just described has several disadvantages when compared to the towel manufactured according to the present invention. Because the tabbing is a manual operation such towels can be very expensive and time consuming to produce. Since they are time consuming it is generally only economical to place one tab 12 at the leading edge. This can be inconvenient since the user may have to inspect both ends of the towel before finding the tab 12. One major difficulty experienced with the prior art tab 12 is that it significantly overlaps the lower adhesive layer 20. In other words, the tab 12 may be as much as ⅛ inch to ¼ inch wider than the adhesive layer 20 or the release layer 18. This is undesirable because it would not be difficult for a user to grab the tab 12 accidentally and inadvertently rip off the adhesive layer 20. The prior art tabs 12 typically comprise a label-like stock having adhesive on the underside. If the tab 12 were not squarely on the towel 22 but were allowed to extend beyond the leading edge 14 then it was found that the tab would stick to other undesired portions of the towel. These and other problems with the prior art towels were overcome by the structure illustrated in FIGS. 2a – 2c.

Figure 2A:
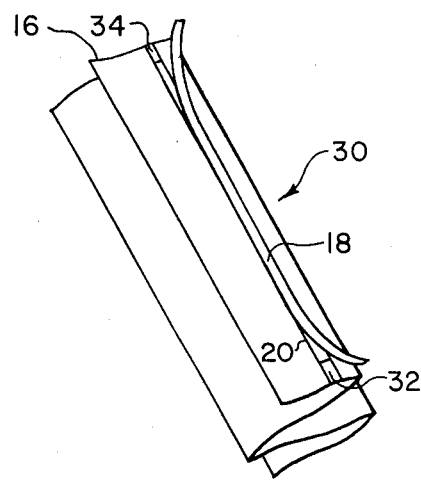
FIG. 2a is a perspective view of the towel manufactured according to a preferred embodiment of the machine of the present invention.

A folded towel 30 manufactured according to the present invention is illustrated in FIG. 2a. Those features that towel 30 has in common with towel 10 are given similar numbers. Towel 30 is like prior art towel 10 in that there is a leading edge tab 32 between the release layer 18 and the adhesive layer 20. In addition, there is a trailing edge tab 34 located at the trailing edge 16 of the towel 30.

Figure 2B:
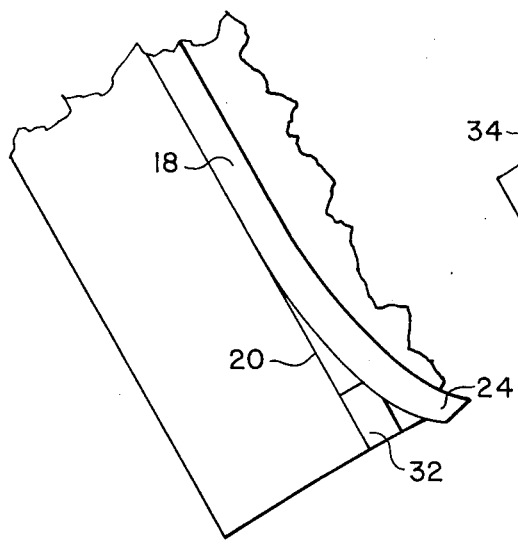

A detail of the leading edge tab 32 is illustrated in FIG. 2b. The tab 32 differs from prior art tab 12 in that it does not extend beyond the sides of the lower adhesive layer 20 or the release layer 18. On the other hand, the width of the leading edge tab 32 is not significantly less than the width of the lower adhesive layer 20 or the top release layer 18. The tab 32 cannot be significantly less than the width of the lower adhesive layer 20 otherwise it looses part of its function as a tab. On the other hand, it cannot be significantly wider than the lower adhesive layer 20 because of the difficulty encountered with wide tabs such as those described as element 12 of the prior art towel 10.

Figure 2C:
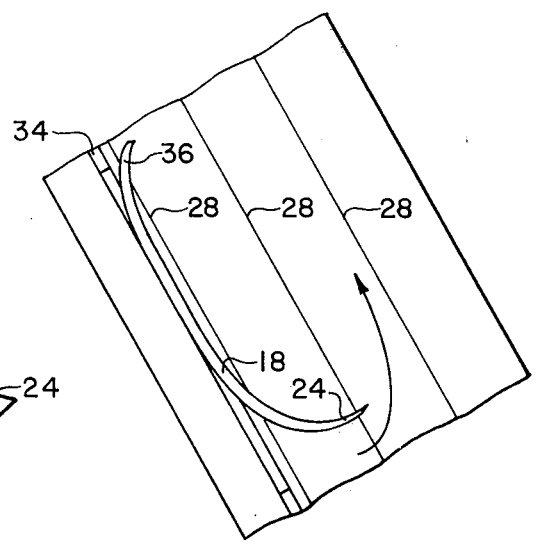
FIG. 2c illustrates the manner in which the release layer is separated from the adhesive layer when attached to a towel.

The towel 30 is prepared for use by grabbing the leading edge 24 and stripping off the release layer 18 in the manner illustrated in FIG. 2c. The stripping operation can be performed in reverse by grabbing the trailing edge 36 of the release layer 18 and pulling the release layer 18 in the opposite direction.

Figure 3:
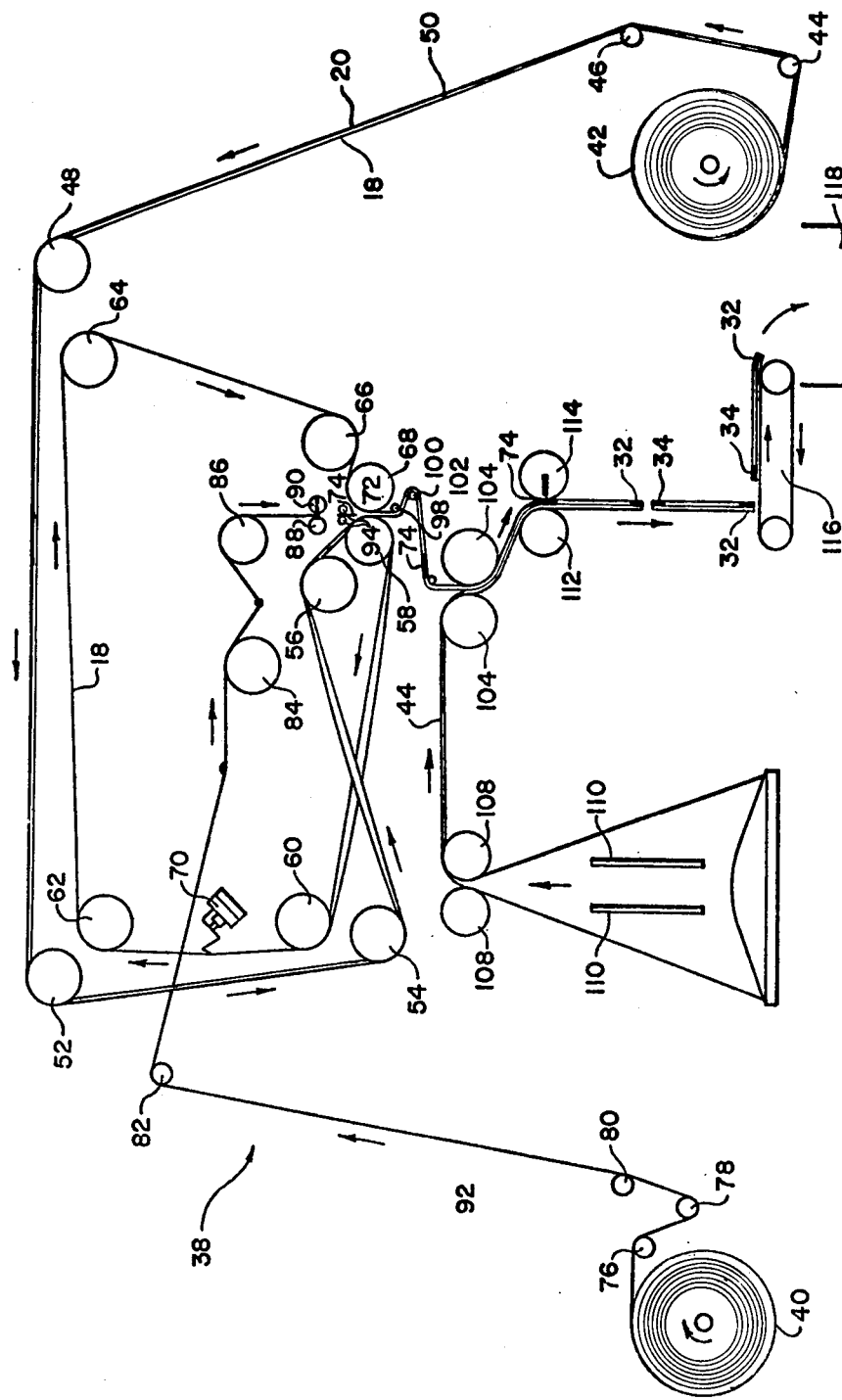
FIG. 3 is a schematic illustration of the towel tabbing machine according to the preferred embodiment of the present invention.

A general schematic illustrating the apparatus and method for forming the towels shown in FIGS. 2a and 2c is illustrated in FIG. 3. The towel tabbing machine 38 is supplied by a roll of tab stock 40, a roll of double sticky backed tape 42 and a source of towel stock webbing 44. Machines for supplying towel stock webbing and for folding the same are known to those of ordinary skill in the art.

According to the preferred embodiment of the present invention the roll of double sticky backed tape 42 passes under dancer roll 44 and over guide roll 46 on its way to upper guide roll 48. The double sticky backed tape comprises an adhesive layer 20 and a release layer 18 similar to that previously described. The adhesive layer 20 has adhesive on both sides thereof and accordingly, is adapted to run on the outside of the roller system of the towel tabbing machine 38. The release paper 18 preferably has a release substance such as silicone on both sides thereof but variations of the present embodiment may be employed such that only a release layer on one side is necessary. Double sticky backed tape is a term often used to refer to this type of adhesive tape. Tape of this sort may be purchased from the Minnesota Mining and Manufacturing Corporation or other suppliers.

The tape 50 supplied from roll 42 first makes contact with the towel tabbing machine 38 at guide roll 48. The tape 50 then passes over outside guide rolls 52 and 54 with the adhesive side 20 always facing outward and away from the roller. Obviously contact between the adhesive and the roller is undesirable due to the drag that it would create. The tape 50 is then twisted and wrapped partially around guide roll 56 and fed to stripper roll 58. Between rolls 54 and 56 the tape is twisted one half turn so that the sticky side 20 faces outward from the roll 56. The function of stripper roll 58 is to separate the release layer 18 from the double sided adhesive layer 20. Adhesive layer 20 continues downwardly but the release layer 18 makes a circuit around rollers 60, 62, 64, 66 and 68 before being reunited on the other side of the adhesive layer 20. According to the preferred embodiment there is a 180° twist in the release layer between stripper roll 58 and guide roll 60. Both rolls 62 and 64 are driven by a conventional chain and sprocket mechanism. A web detecting limit switch 70 is employed to detect breaks in the release layer 18. If for some reason the release layer 18 is not detected by limit switch 70, then limit switch 70 cuts off power to the whole machinery. Breaks in the release layer 18 and therefore in the adhesive tape 50 often occur where rolls of adhesive tape 50 have been previously spliced together.

A nip is formed between separating roller 58 and roll 68 where the adhesive layer 20 is reunited with release layer 18. The nip point 72 is the location at which a tab 74 is inserted. The tab 74 is cut from tab stock roll 40 which is fed over rolls 76, 78, 80, 82, 84, and 86 to a tab cutting mechanism 88 and 90. Roll 78 is a dancer roll which serves to take up the slack in the tab stock. Roll 78 operates in much the same fashion as roll 44 operates with respect to the adhesive tape stock 50. Roll 76, 80, 82, 84 and 86 otherwise serve to guide the tab stock to the cutting location.

The tab stock 92 is cut into tabs 74 by means of rotating anvil 88 and rotating knife 90. The cutting mechanism 88 and 90 is of a sort well known to those of ordinary skill in the art. Once the tab 74 has been cut by cutting mechanism 88 and 90 it is guided via a pair of small guide rolls 94 into the nip 74 formed between the adhesive layer 20 and the release layer 18 as they are guided by stripping roll 58 and roll 68. The reunited tape 96 then passes over a plurality of roller pins 98, 100 and 102 and then into a pair of applying rollers 104. As illustrated in FIG. 3 the reunited tape 96 includes between the adhesive layer 20 and the release layer 18 the sandwiched tab 74. At applying rollers 104 the reunited tape 96 is combined with folded towel web stock 44. The folded stock 44 is fashioned in a manner known to those of ordinary skill in the art. A roll of webbing runs over a guide bar 106 and up to a pair of press rolls 108. A set of folding guide bars 110 put the folds illustrated as element 28 in FIGS. 1 through 2c into the longitudinal width of the towel. The folded stock 44 is then fed to applying rollers 104 where it is combined with reunited tape 96. In this manner the reunited tape 96 is applied continuously and longitudinally to the folded towel webbing 44. From applying rollers 104 the towel and tape combination is fed into cutting mechanism 112 and 114. Roll 112 acts as an anvil against which a knife in roll 114 operates. The towel tabbing machine 38 includes a conventional differential gear mechanism which is employed to change the phase of the tab cut off mechanism 88 and 90 with respect to the towel cut off mechanism 112 and 114. The differential gear allows 360° of phase adjustment between the tab cut off mechanism and the towel cut off mechanism. Accordingly the towel may be cut substantially transversely at any location with respect to the sandwiched tab 74. In the preferred embodiment of the present invention it is desirable to cut the towel at the mid point of the tab. By cutting the towel in half at the mid point of the tab 74 two new separate equal tabbed sections are automatically formed. Those tabbed sections are, of course, the leading edge tab 32 of one towel and the trailing edge tab 34 of the preceding towel. According to the preferred embodiment of the present invention the uncut tabs 74 are typically about a 1½ inches long. Therefore when the tabs 74 are cut the leading edge tab 32 and the trailing edge tab 34 are approximately ¾ inch in length. The tape used is about ½ inch wide and the towels according to the preferred embodiment of the present invention measure approximately 36 inches long in their cut condition.

The cut towels 34 are then delivered to a conveyor 116 and subsequently packed into conventional sanitized shipping cartons 118.

Figure 4:
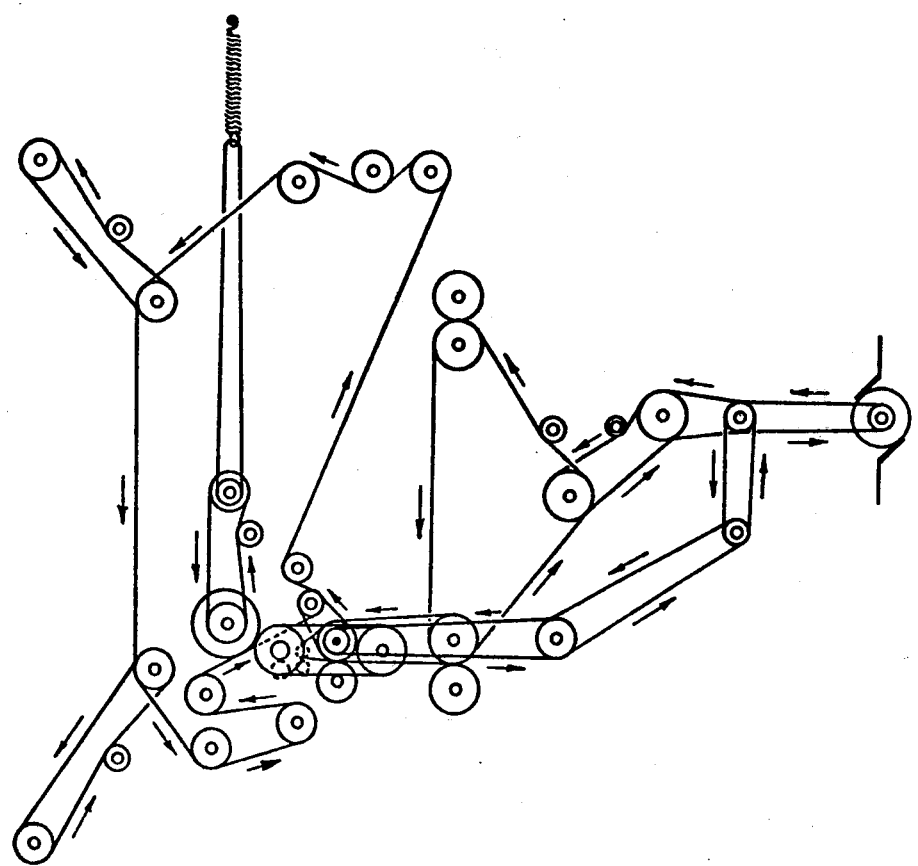
FIG. 4 is a general schematic of the drive train associated with the towel tabbing machine illustrated in FIG. 3.

The drive train mechanism associated with the towel tabbing machine 38 is illustrated in general detail in FIG. 4. The drive mechanism itself is not deemed to be an especially important feature of the present invention and the construction of the drive train is believed to be well within the skill of those familiar with the art. Accordingly, the details of the drive mechanism will not be explained with greater specificity. The entire mechanism can be driven off one prime mover. Therefore, by using appropriate combinations of sprockets and chain drives it is possible to achieve uniform timing of the machine elements. The only major feature of importance in the drive mechanism is the differential gear device 120 used to adjust the phase between the tab cutting mechanism 88 and 90 and the towel cutting mechanism 112 and 114.

The foregoing comprises a preferred embodiment of the present invention. However, other modifications and changes would be well within the spirit and scope of the invention. For example, the present invention comprehends the removal of the release layer 18 from the double backed adhesive layer 20 and the reunification of the release layer 18 with the adhesive 20 on the other side of the adhesive 20 from which it originally started. This particular technique was found to be advantageous in view of the space requirements of the machine. However, it will be clear to those of ordinary skill in the art that the release layer and the adhesive layer could be delaminated and then reunited on the same side of the tape if necessary or desirable.

The release layer 18 according to the preferred embodiment has a glossy release side and a non-glossy side to it. It would be obvious to one of ordinary skill in the art to use a release layer which is glossy on both sides if the circumstances required it.

The adhesive stock 50 is made to travel a fairly long circuit as is the release liner 18 once it is stripped from the adhesive backing. The extra travel around the guide rollers helps the tape to absorb nearly instantaneous stops and starts. In actuality the liner 18 or the tape 15 will stretch a bit when a load is placed upon it. The longer the distance between locations of applied force, the greater the ability of the tape to absorb the shocks. Therefore it was found highly useful to cause the tape to travel a relatively great distance between points of loading. It will be recognized by those of ordinary skill in the art that such a damping mechanism may not be necessary under all circumstances.

The inserted tabs can be of virtually any desirable length. The tabs should not be so small that a purchase cannot be readily achieved on the release layer 18. On the other side of the coin the tab 32 or 34 should not be so long as to cause the unsecured portion 24 or 36 to dangle unnecessarily. According to the preferred embodiment the cut tabs may be ¾ inch long or may be as short as ⅜ inch or less depending upon the circumstances.

The term double sticky backed tape has been used to describe the delaminated tape 50 which includes a release layer 18 and a double sided adhesive layer 20. The same type of tape is also referred to in the trade as double faced tape.

While the invention has been described with reference to a preferred embodiment it will be clear to those of ordinary skill in the art that various different changes and modifications can be made without departing from the spirit and scope of the invention.

I claim:
1. A tabbing machine comprising:
   a source of adhesive tape having a release layer and an adhesive layer having adhesive on both sides thereof;
   means for separating said adhesive layer from said release layer;
   means for inserting a tab between said separated adhesive layers and said release layer;
   means for reuniting said adhesive layer and said release layer; and,
   means for cutting substantially transversely through said reunited tape and said tab at the location where said tab was inserted.
2. A tabbing machine comprising:
   a source of double backed adhesive tape having a release layer and an adhesive layer having adhesive on both sides thereof;
   separating means for separating said adhesive layer from said release layer;
   tab inserting means for inserting a tab between said adhesive layer and said release layer;
   reuniting means for reuniting said adhesive layer and said release layer; and,
   cutting means for cutting substantially transversely through said reunited tape and said tab at the location where said tab was inserted.
3. The machine of claim 1 further including:
   a towel folding means for forming surgical type towels; and,
   a means for applying said reunited tape to said surgical towels before said tape is cut.
4. The machine of claim 1 wherein
   said adhesive layer has a first and a second side, said release paper being originally located on said first side but reunited to said adhesive layer on said second side.

5. The machine of claim 1 further including:
a timing adjustment means for adjusting the movement of said cutting means relative to said tab inserting means.

6. A method for tabbing a tape comprising the steps of:
separating the adhesive layer of a double backed adhesvie tape from its release layer;
inserting a tab between said adhesive layer and said release layer;
reuniting said release layer and said adhesive layer to form a reunited tape with said tabs sandwiched between said layers; and,
cutting substantially transversely through said reunited tape and said web at the location of said tab.

7. The method of claim 6 further including the step of:
attaching said reunited tape to a surgical towel prior to cutting said tape.

8. A tabbing machine comprising:
a means for separating the adhesive layer from the release layer of an adhesive tape;
means for inserting a tab between said separated adhesive layer and said release layer;
means for reuniting said adhesive layer and said release layer; and,
means for cutting substantially transversely through said reunited tape and said tab at the location where said tab was inserted.

9. A tabbing machine comprising:
a means for inserting a tab between a double backed adhesive layer and a release layer;
means for uniting said adhesive layer with said release layer;
means for attaching said double backed adhesive layer to a towel-like material; and,
means for cutting substantially transversely through said towel material and said tab and said double backed adhesive layer at the location where said tab was inserted.

* * * * *